(12) United States Patent
Chen et al.

(10) Patent No.: US 8,366,731 B2
(45) Date of Patent: Feb. 5, 2013

(54) ARTIFICIAL HAIR TRANSPLANTATION METHOD

(75) Inventors: Ming-Jeng Chen, New Taipei (TW);
Yen-Chih Chen, New Taipei (TW);
Peng-Yu Chen, New Taipei (TW)

(73) Assignee: Ming-Jeng Chen, New Taipei (TW)

( * ) Notice: Subject to any disclaimer, the term of this patent is extended or adjusted under 35 U.S.C. 154(b) by 21 days.

(21) Appl. No.: 13/104,814

(22) Filed: May 10, 2011

(65) Prior Publication Data
US 2012/0289986 A1 Nov. 15, 2012

(51) Int. Cl.
*A61B 17/34* (2006.01)
(52) U.S. Cl. ................................................ 606/187
(58) Field of Classification Search .......... 606/131, 606/133, 185, 187; 623/15.11
See application file for complete search history.

(56) References Cited

U.S. PATENT DOCUMENTS

| 3,858,245 | A | * | 1/1975 | Nate et al. | 128/898 |
| 3,914,801 | A | * | 10/1975 | Dick et al. | 128/898 |
| 4,027,675 | A | * | 6/1977 | Colone | 606/187 |
| 4,221,212 | A | * | 9/1980 | Miller | 606/187 |
| 4,254,772 | A | * | 3/1981 | McNamee | 606/187 |
| 4,588,408 | A | * | 5/1986 | Yamada | 623/15.11 |
| 5,330,530 | A | * | 7/1994 | Hastings | 128/898 |
| 5,578,054 | A | * | 11/1996 | Arnold | 606/185 |
| 6,468,288 | B1 | * | 10/2002 | Manning | 606/187 |

* cited by examiner

*Primary Examiner* — Ryan Severson
*Assistant Examiner* — Jonathan W Miles
(74) *Attorney, Agent, or Firm* — Muncy, Geissler, Olds & Lowe, PLLC

(57) ABSTRACT

An artificial hair transplantation method for implanting, directly or indirectly, artificial chemically synthesized filaments into the epidermal layer and the dermal layer of the human scalp features painless incisions and allows hair restoration to be attained in a short period of time, such as a few hours.

18 Claims, 9 Drawing Sheets

(a)

(b)

(c)

(a)

(b)

ARTIFICIAL HAIR TRANSPLANTATION METHOD

FIELD OF THE INVENTION

The present invention relates to artificial hair transplantation methods, and more particularly, to an artificial hair transplantation method for performing hair transplantation by implanting artificial chemically synthesized filaments into the epidermal layer and the dermal layer of the human scalp.

BACKGROUND OF THE INVENTION

Hair not only protects the surface of the skin but serves an esthetic purpose. Hair grows from hair follicles found all over the skin. The hair follicle, a gland-equipped sac-like structure, takes root in the dermis and extends upward to reach the epidermis; hence, the hair follicle consists of a dermal portion and an epidermal portion. The dermal portion of the hair follicle comprises dermal papillae (DP) and a dermal sheath (DS). The epidermal portion of the hair follicle comprises an inner root sheath (IRS) and an outer root sheath (ORS). The human scalp is the skin that covers the top of the human head and, of course, comprises the dermis and the epidermis.

Hair growth is a continuous lifelong process that takes place in cycles of four phases: anagen (growth), catagen (regression), telogen (rest), and exogen (shedding). A prolongation of the telogen phase, coupled with the ensuing failure to enter a new anagen phase, is a proven pathological cause of alopecia (hair loss) of an extent from hair thinning to baldness. Alopecia brings about psychological problems in both men and women. The symptoms can include loss of self-esteem, anxiety, fear and negative body image.

To mitigate alopecia, the prior art effectuates hair restoration by follicular unit transplantation (FUT) which involves: removing from the occipital portion of the human scalp a long, thin donor strip; performing stereo-microscopic dissection on the strip to remove individual follicular units therefrom; and implanting the individual follicular units in the recipient area of the human scalp. However, FUT has its own drawbacks. For example, FUT leaves a linear donor scar in the donor area of the human scalp. The drawback is overcome by a subsequent hair restoration technique known as follicular unit extraction (FUE). FUE does not leave any visible scar in the donor area of the human scalp, as FUE uses a biopsy punch to remove individual follicular unit grafts from the occipital portion and temporal portions of the human scalp. The advantage that the FUE method has over FUT is that FUE does not leave a linear donor scar, causes less bleeding, and causes less post-operative discomfort. However, FUE has its own drawbacks. For example, FUE is time-consuming, expensive, and is not suitable for patients who require transplantation of a large number of hair follicular units. Furthermore, not only does the success of FUE largely depend on the experience of the hair transplant team, but FUE is notorious for a likelihood of an increased risk of follicular damage in extraction which can lead to sub-optimal growth of the hair transplant.

Accordingly, it is imperative to develop a hair restoration technique that overcomes the aforesaid drawbacks of the prior art.

SUMMARY OF THE INVENTION

It is an objective of the present invention to provide an artificial hair transplantation method for implanting, directly or indirectly, artificial chemically synthesized filaments into the human scalp so as to effectuate hair restoration in a short period of time, such as a few hours.

Another objective of the present invention is to provide an artificial hair transplantation method for implanting directly or fixing the artificial chemically synthesized filaments to above the human scalp by means of a needle so as to effectuate hair transplantation.

Yet another objective of the present invention is to provide an artificial hair transplantation method for implanting the artificial chemically synthesized filaments to above the human scalp indirectly by means of a needle, using a fixing thread, so as to effectuate hair transplantation.

In order to achieve the above and other objectives, the present invention provides an artificial hair transplantation method for performing hair transplantation limited to an epidermal layer and a dermal layer of a human scalp, the method comprising the steps of: providing an artificial chemically synthesized filament; providing a needle for pulling the artificial chemically synthesized filament and driving the artificial chemically synthesized filament to enter the human scalp and lie flatly in the epidermal layer or the dermal layer, and driving the needle to leave the epidermal layer or the dermal layer and stay above the human scalp such that the needle separates from the epidermal layer or the dermal layer, wherein the needle enables the artificial chemically synthesized filament to be present in the epidermal layer and the dermal layer simultaneously; and crossing and knotting the artificial chemically synthesized filament above the human scalp so as to form a knot at an appropriate point of the artificial chemically synthesized filament, followed by fixing the artificial chemically synthesized filament to the human scalp.

In order to achieve the above and other objectives, the present invention provides an artificial hair transplantation method for performing hair transplantation limited to an epidermal layer and the dermal layer of a human scalp, the method comprising the steps of: providing an artificial chemically synthesized filament and a fixing thread; providing a needle for pulling the fixing thread in a manner that movement of the needle alternates between entering the epidermal layer and the dermal layer from outside the human scalp and exiting the epidermal layer and the dermal layer to thereby leave the human scalp, wherein the fixing thread comprises a plurality of exposed portions above the epidermal layer, such that a plurality of spaces are formed between the epidermal layer and the exposed portions of the fixing thread, respectively; and passing the artificial chemically synthesized filaments through the spaces, followed by knotting the artificial chemically synthesized filaments in a manner that the knots thus formed are fixed to the fixing thread, thereby allowing the artificial chemically synthesized filaments to be fixed to the human scalp by means of the fixing thread.

Unlike the prior art, the present invention provides an artificial hair transplantation method for implanting artificial chemically synthesized filaments into the epidermal layer and the dermal layer of the human scalp. According to the present invention, the artificial chemically synthesized filaments are positioned at a depth of 0.1 mm to 0.7 mm in the epidermal layer when implanted, wherein the dermal layer is 3 to 5 times thicker than the epidermal layer; in other words, the artificial chemically synthesized filaments thus implanted in the human scalp are not deep at all, as they can be just 0.4 mm deep in the human scalp, for example. With the implanted artificial chemically synthesized filaments being confined to the epidermal layer and the dermal layer, the filament-receiving holes opened in the human scalp by the surgeon during the hair transplantation process are small and shallow and thus cause relatively little pain to the hair transplantation patient.

Given a filament recipient area of just 1 cm² to 3 cm², hair restoration can be accomplished in a short period of time, such as a few hours. The artificial chemically synthesized filaments proposed by the present invention are of high strength and high fidelity, and are implanted into the human scalp by means of a therapeutic needle; hence, the artificial hair transplantation method of the present invention reduces transplant rejection and infection. Accordingly, the artificial hair transplantation method of the present invention is effective in hair restoration and hair replacement.

BRIEF DESCRIPTION OF THE DRAWINGS

To enable persons skilled in the art to fully understand the objectives, features, and advantages of the present invention, the present invention is hereunder illustrated with specific embodiments in conjunction with the accompanying drawings, in which.

DETAILED DESCRIPTION OF THE PREFERRED EMBODIMENTS

Figure 1:
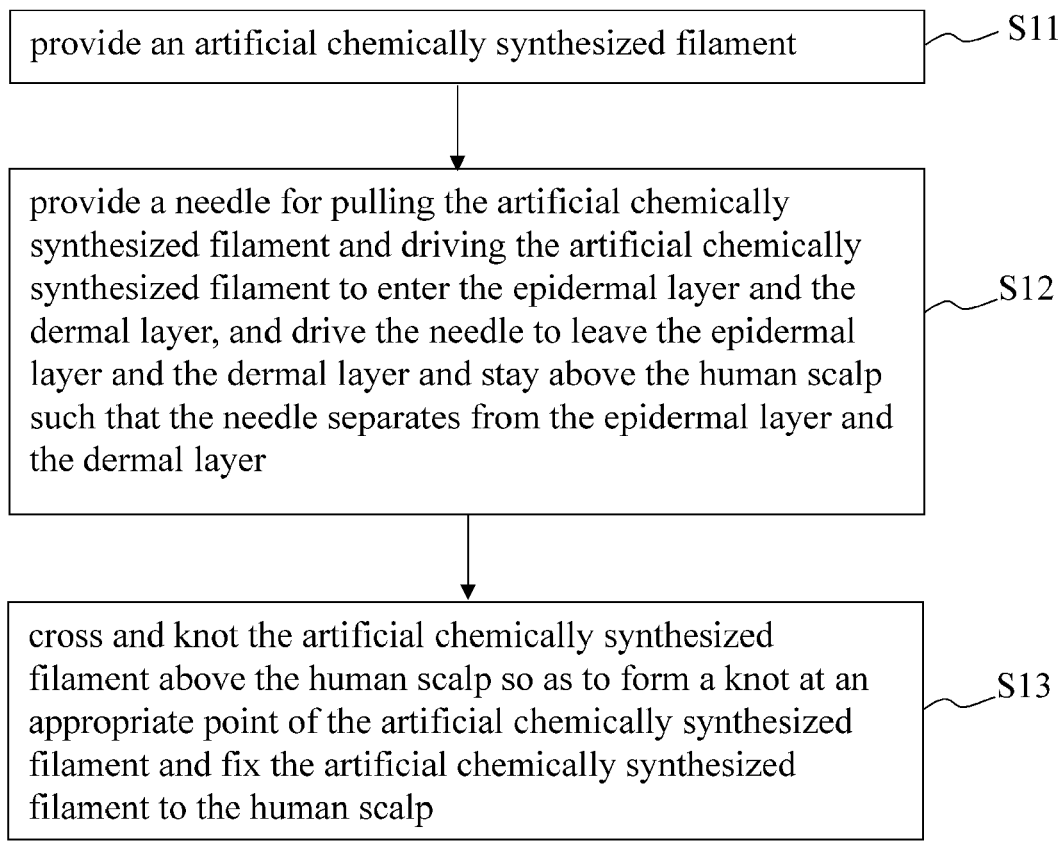
FIG. 1 is a flowchart of implanting an artificial chemically synthesized filament into a human scalp according to an embodiment of the present invention.
Figure 2:
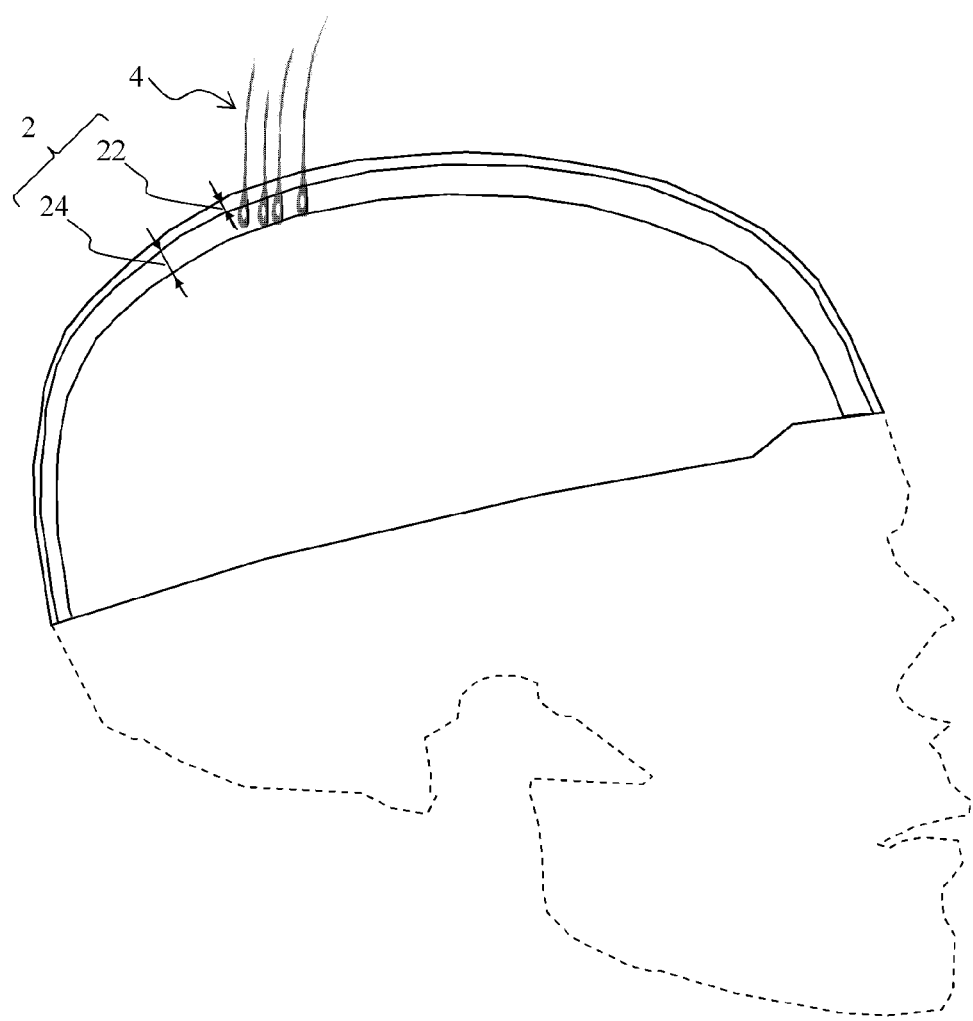
FIG. 2 is a cross-sectional view of the human scalp mentioned in FIG. 1.

Referring to FIG. 1, there is shown a flowchart of implanting an artificial chemically synthesized filament into a human scalp according to an embodiment of the present invention. As shown in FIG. 1, an artificial hair transplantation method of the present invention entails implanting an artificial chemically synthesized filament into the epidermal layer and the dermal layer of the human scalp. In an embodiment, the artificial chemically synthesized filament is of a thread diameter of 0.08 mm. Referring to FIG. 2, there is shown a cross-sectional view of an artificial chemically synthesized filament 4 implanted into a human scalp 2 in order to effectuate hair transplantation according to an embodiment of the present invention, wherein the human scalp 2 further comprises an epidermal layer 22 and a dermal layer 24.

The process flow of the artificial hair transplantation method according to an embodiment of the present invention starts with step S11. Step S11 involves providing the artificial chemically synthesized filament 4. The artificial chemically synthesized filament 4 is made of at least one of green & white polyfilament chemical absorbable suture (EU-TEK/PGA), violet polyfilament chemical absorbable suture (Violet), plain catgut, chromic catgut, monofilament nylon, braided nylon, Unilene polypropylene suture, polyester suture, wire, silk, and twisted silk.

Afterward, step S12 entails providing a needle for pulling the artificial chemically synthesized filament 4 and driving the artificial chemically synthesized filament 4 to enter the human scalp 2 and lie flatly in the epidermal layer 22 and the dermal layer 24, and driving the needle to leave the epidermal layer 22 and the dermal layer 24 to stay above the human scalp 2 such that the needle separates from the epidermal layer 22. In doing so, the needle enables the artificial chemically synthesized filament 4 to be present in the epidermal layer 22 and the dermal layer 24 simultaneously. Alternatively, it is also feasible to allow the artificial chemically synthesized filament 4 to be present in the epidermal layer 22 only. The needle is at least one of a reverse cutting needle, a regular cutting needle, a diamond point needle, and a premium reverse cutting.

Figure 3:
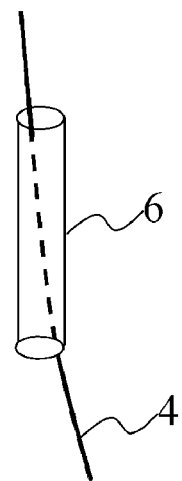
FIG. 3 is a schematic view of engagement between the artificial chemically synthesized filament and a needle according to different exemplary embodiments of the present invention.
Figure 3:
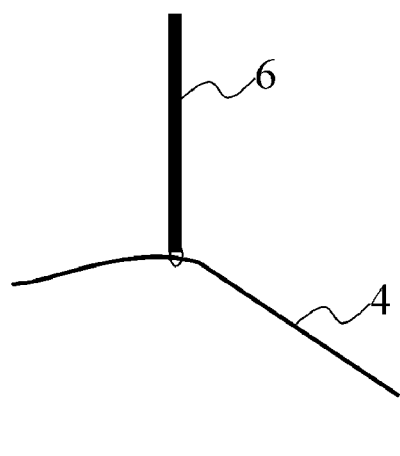
Figure 3:
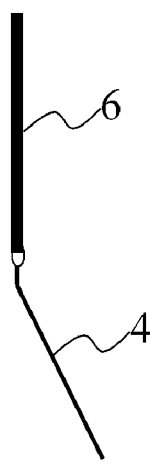

Referring to FIG. 3, there is shown a schematic view of engagement between the artificial chemically synthesized filament 4 and a needle 6 according to different exemplary embodiments of the present invention. As shown in the drawing, the engagement is effectuated in three different ways: (a) providing a hollow needle that has therein a receiving space and functions as the needle 6, followed by passing the artificial chemically synthesized filament 4 through the receiving space such that the artificial chemically synthesized filament 4 is held therein; (b) providing a one-eyed needle that functions as the needle 6, followed by passing the artificial chemically synthesized filament 4 through the eye at one end of the one-eyed needle in a manner to enable engagement of the one-eyed needle and the artificial chemically synthesized filament 4; and (c) providing a lead that functions as the needle 6, followed by connecting the lead and the artificial chemically synthesized filament 4 such that the artificial chemically synthesized filament 4 enters the epidermal layer 22 and the dermal layer 24, wherein the lead can be a stainless steel wire.

Figure 4:
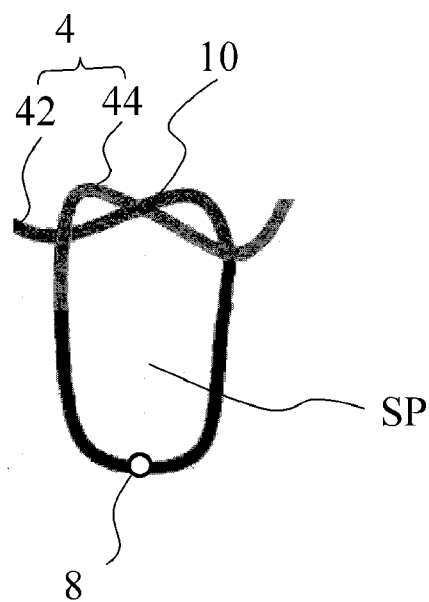
FIG. 4 is a schematic view of the engagement between the needle and the artificial chemically synthesized filament shown in FIG. 3.
Figure 4:
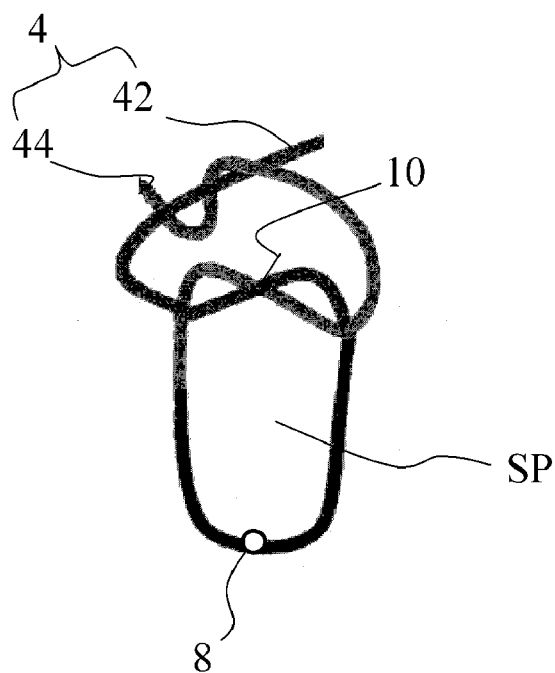

Afterward, step S13 entails crossing and knotting the artificial chemically synthesized filament 4 above the human scalp 2 so as to form a knot 10 at an appropriate point of the artificial chemically synthesized filament 4, wherein the appropriate point of the artificial chemically synthesized filament 4 is, for example, close to the human scalp 2, followed by fixing the artificial chemically synthesized filament 4 in place at the human scalp 2. An exemplary way of knotting is depicted in FIG. 4. For the sake of brevity and clarity, the artificial chemically synthesized filament 4 is, in an exemplary embodiment, divided by a midpoint 8 into a first synthetic filament 42 and a second synthetic filament 44. As shown in FIG. 4, the exemplary way of knotting comprises two steps of: (a) pressing the first synthetic filament 42 against the second synthetic filament 44, followed by bending the first and second synthetic filaments 42, 44 over each other to form the knot 10 by a single knotting process and thereby form an enclosed space SP defined by the first and second synthetic filaments 42, 44 together, wherein the knot 10 and the enclosed space SP together enable the artificial chemically synthesized filament 4 to be fixed to the epidermal layer 22 and the dermal layer 24; and (b) knotting, after forming the knot 10, the artificial chemically synthesized filament 4 repeatedly to reinforce the implantation of the artificial chemically synthesized filament 4 in the human scalp 2.

A point to note is that step S12 further entails pushing the needle into the epidermal layer 22 and the dermal layer 24 to reach a predetermined depth therein, wherein the predetermined depth ranges between 0.1 mm and 4 mm. The beneficial outcome of the artificial hair transplantation method of the present invention as implemented by steps S11 through S13 is that, when implanted into the human scalp 2, every one said artificial chemically synthesized filament 4 consists of the first synthetic filament 42 and the second synthetic filament 44 which are inherently joined by the knot 10. Each of the first synthetic filament 42 and the second synthetic filament 44 is of a length substantially equal to a half of that of the artificial chemically synthesized filament 4. As a result, upon completion of the hair transplantation carried out by the artificial hair transplantation method of the present invention, the total number of the first synthetic filaments 42 and the second synthetic filaments 44 is two times that of the artificial chemically synthesized filaments 4.

Figure 5:
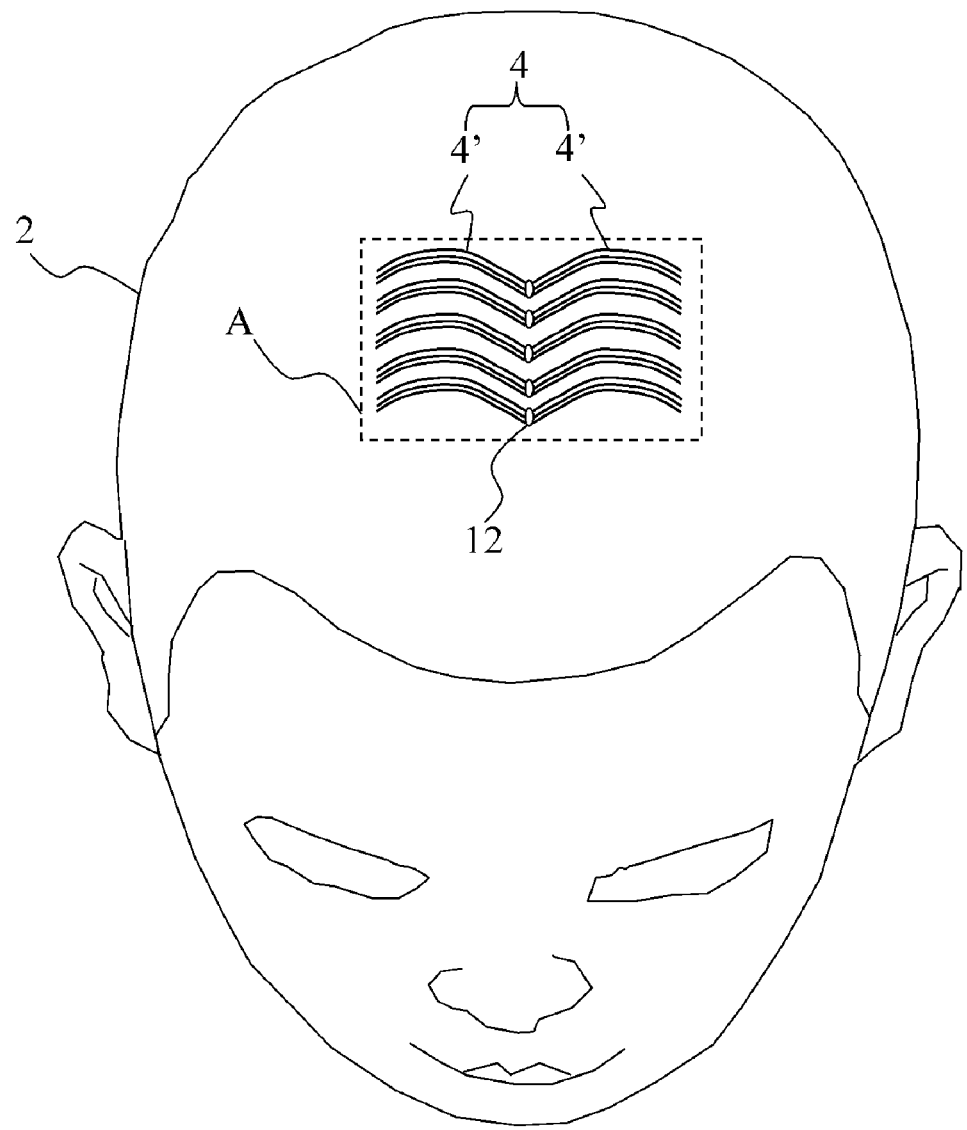
FIG. 5 is a schematic view of the arrangement of the artificial chemically synthesized filaments implanted according to the process flow described in FIG. 1.

Patients who need implantation of the artificial chemically synthesized filaments into the human scalp benefit from the artificial hair transplantation method of the present invention, because the artificial chemically synthesized filaments are implanted into the human scalp in a pattern corresponding to the distribution pattern of a plurality of hair follicles (spaced apart from each other by a distance ranging between 2 mm and 4 mm) in the dermal layer 24 according to an embodiment of the present invention. A plurality of said artificial chemically synthesized filaments 4 are fixed to positions (hereinafter referred to as pseudo hair follicles 12 as shown in FIG. 5) above the human scalp, such that the artificial chemically synthesized filaments 4 thus implanted mimic the innate hair of the human scalp in terms of the respective positions and the pattern of arrangement of hair follicles of the human scalp. Fixed to each of the pseudo hair follicles 12 are the plurality of artificial chemically synthesized filaments 4 spaced apart from each other by a distance that ranges between 0.5 mm and 1.5 mm.

Referring to FIG. 5, there is shown a schematic view of the arrangement of the artificial chemically synthesized filaments 4 implanted according to the process flow described in FIG. 1. As shown in FIG. 5, in an embodiment of the present invention, to perform hair transplantation at the positions of the pseudo hair follicles 12 (spaced apart from each other by a distance ranging between 1 mm and 1.5 mm) in a hair transplantation zone A, it is feasible to implant three said artificial chemically synthesized filaments 4 into the epidermal layer 22 of the human scalp 2 in a manner that three said artificial chemically synthesized filaments 4 thus implanted correspond in position to, that is, being close to, a corresponding one of the pseudo hair follicles 12, and then repeat the aforesaid procedure until all of the pseudo hair follicles 12 in the hair transplantation zone A are treated by the aforesaid procedure. By performing the aforesaid knotting technique described in step S13 on the artificial chemically synthesized filaments 4 implanted at the positions of the pseudo hair follicles 12, respectively, three said artificial chemically synthesized filaments 4 appear in the form of six said half synthetic filaments 4'.

Figure 6:
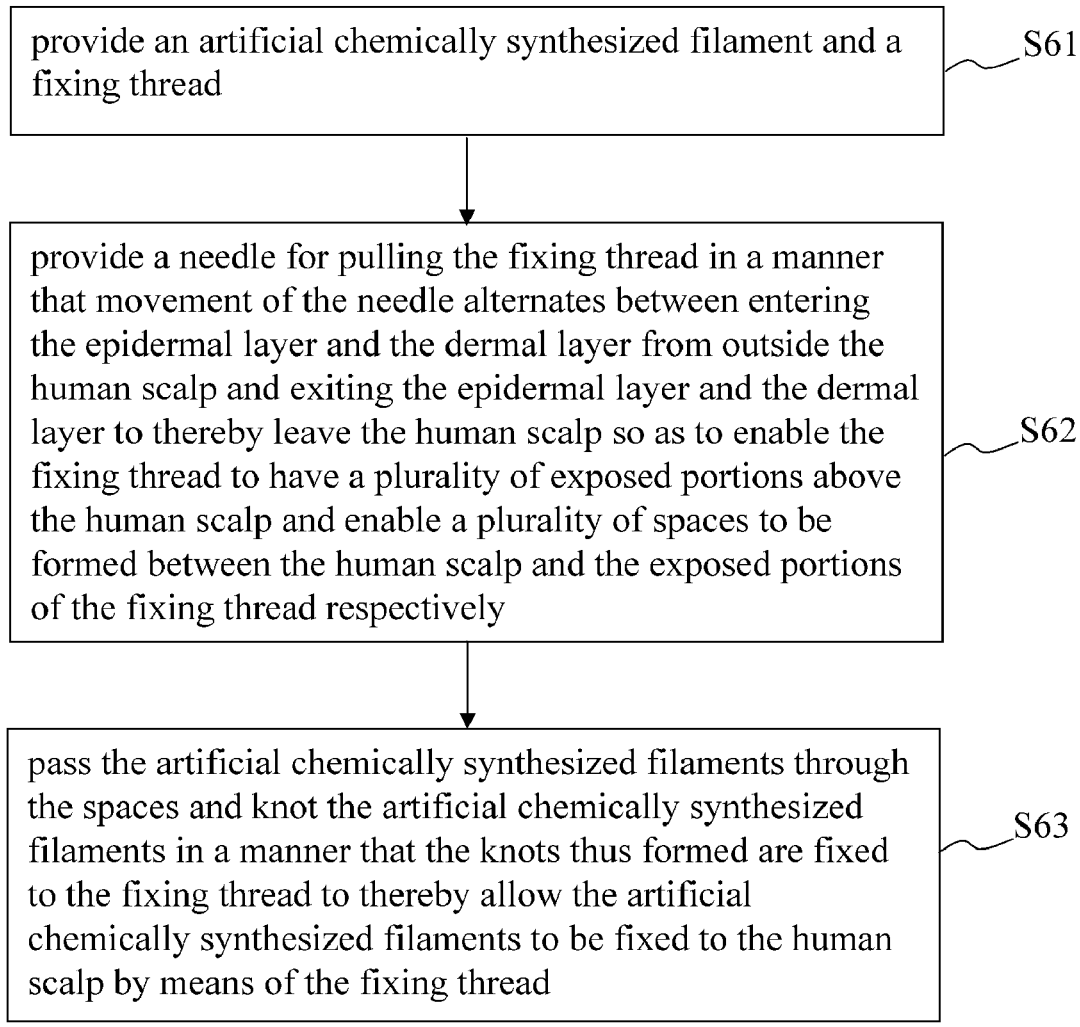
FIG. 6 is a flowchart of implanting an artificial chemically synthesized filament into a human scalp according to another embodiment of the present invention.

Referring to FIG. 6, there is shown a flowchart of implanting the artificial chemically synthesized filament 4 into the human scalp 2 according to another embodiment of the present invention. As shown in FIG. 6, the artificial hair transplantation method whereby the artificial chemically synthesized filaments 4 are implanted into the epidermal layer 22 and the dermal layer 24 of the human scalp 2 comprises the steps S61 through S63. Step S61 entails providing the artificial chemically synthesized filaments 4 and a fixing thread 14.

The artificial chemically synthesized filaments 4 and/or the fixing thread 14 are/is made of at least one of green & white polyfilament chemical absorbable suture (EU-TEK/PGA), violet polyfilament chemical absorbable suture (Violet), plain catgut, chromic catgut, monofilament nylon, braided nylon, Unilene polypropylene suture, polyester suture, wire, silk, and twisted silk.

Step S62 entails providing a needle 6 for pulling the fixing thread 14 in a manner that the movement of the needle 6 alternates between entering the epidermal layer 22 and the dermal layer 24 from outside the human scalp 2 and exiting the epidermal layer 22 and the dermal layer 24 to thereby leave the human scalp 2. As a result, the fixing thread 14 comprises an exposed portion above the human scalp 2 and a hidden portion inside the epidermal layer 22 and the dermal layer 24, wherein the exposed portion and the hidden portion alternate. As a result, a plurality of spaces S (see FIG. 8) are formed between the human scalp 2 and the exposed portions of the fixing thread 14, respectively. The needle is at least one of a reverse cutting needle, a regular cutting needle, a diamond point needle, and a premium reverse cutting.

Step S63 entails passing the artificial chemically synthesized filaments 4 through the spaces S, followed by knotting the artificial chemically synthesized filaments 4 in a manner that the knots 10 thus formed are fixed to the fixing thread 14, thereby allowing the artificial chemically synthesized filaments 4 to be fixed to the human scalp 2 by means of the fixing thread 14.

The hidden portions of the fixing thread 14 are 0.1 mm to 4 mm deep in the human scalp 2 and are spaced apart from each other by a distance that ranges between 0.1 mm and 10 mm. The exposed portions of the fixing thread 14 are spaced apart from each other by a distance that ranges between 2.5 mm and 25 mm. In another embodiment, the exposed portions of the fixing thread 14 are spaced apart from each other by a distance that ranges between 0.5 mm and 1.5 mm. The aforesaid distances that separate the hidden portions of the fixing thread 14 enable sufficient air ventilation immediately above the recipient area of the human scalp 2 after hair transplantation.

Figure 7:
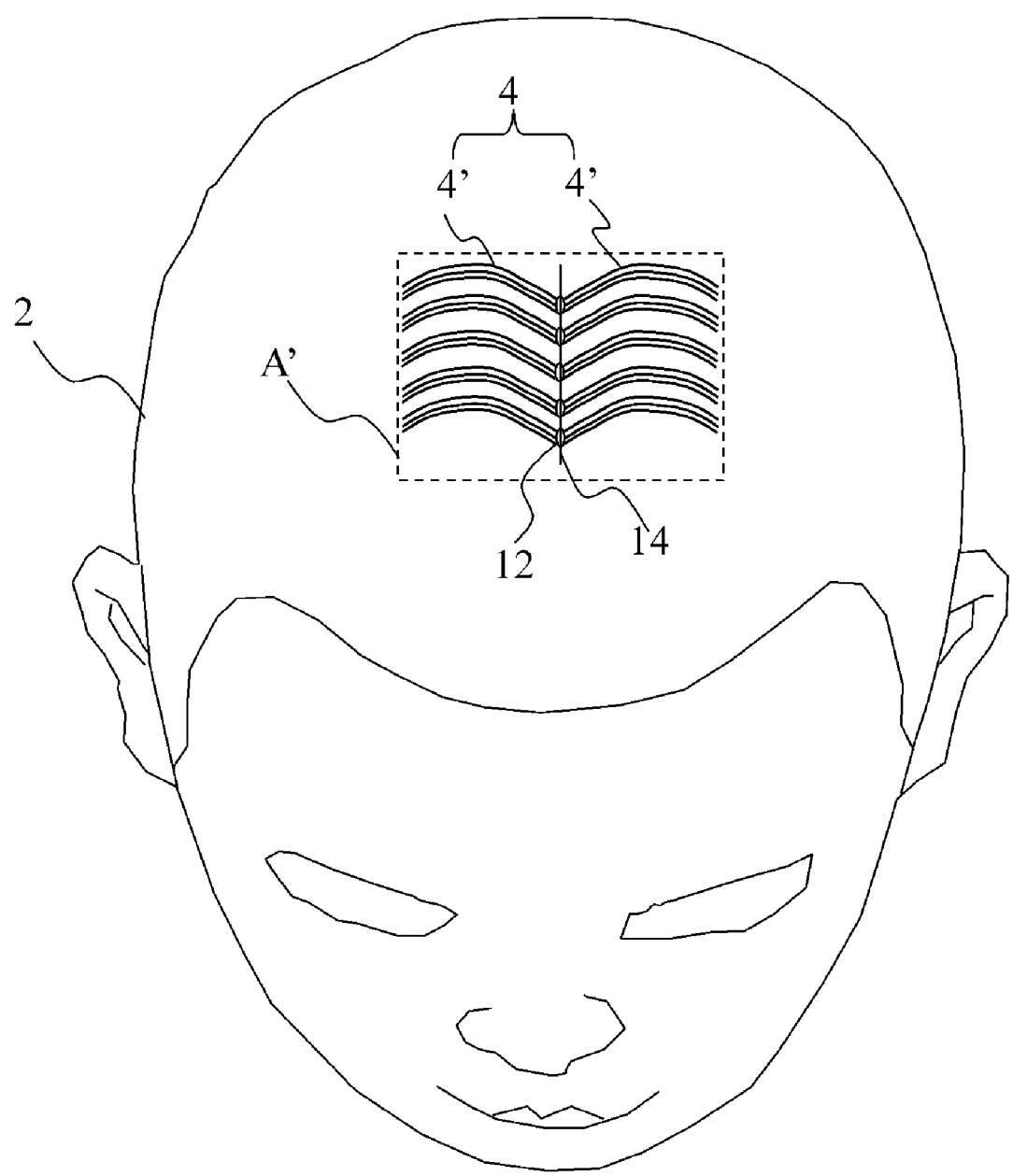
FIG. 7 is a schematic view of the arrangement of the artificial chemically synthesized filaments implanted according to an embodiment of the present invention.

Referring to FIG. 7, there is shown a schematic view of the arrangement of the artificial chemically synthesized filaments 4 implanted according to an embodiment of the present invention. As shown in FIG. 7, in an embodiment of the present invention, to perform hair transplantation at the positions of the pseudo hair follicles 12 (spaced apart from each other by a distance ranging between 1 mm and 1.5 mm) in a hair transplantation zone A', it is feasible to fix the fixing thread 14 to above the human scalp 2, knot the artificial chemically synthesized filaments 4 with the aforesaid knotting technique to enable the artificial chemically synthesized filaments 4 to be fixed to the fixing thread 14, and implant three said artificial chemically synthesized filaments 4 at the positions of the pseudo hair follicles 12. After the artificial chemically synthesized filaments 4 form their respective knots 10 which are positioned at the positions of the pseudo hair follicle 12, three said artificial chemically synthesized filaments 4 appear in the form of six half synthetic filaments 4'.

Figure 8:
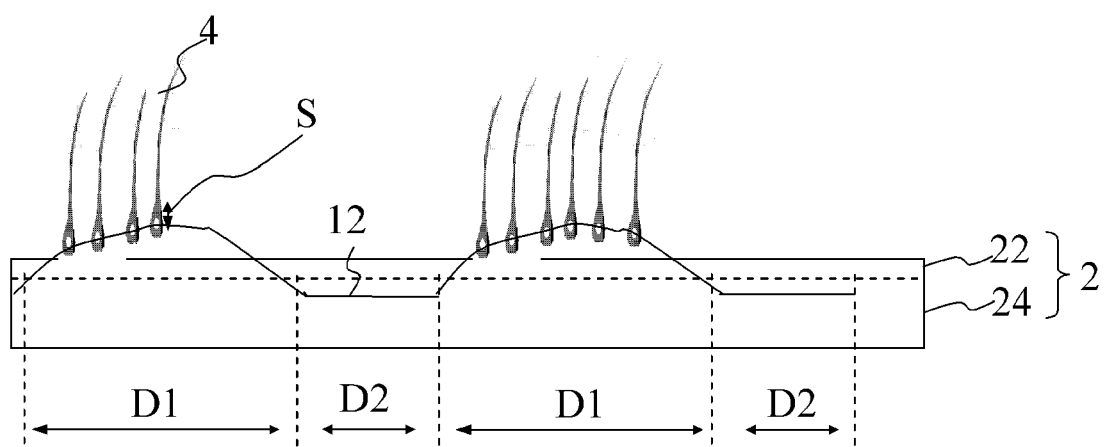
FIG. 8 is a schematic view of the artificial chemically synthesized filaments implanted according to the process flow described in FIG. 6.

Referring to FIG. 8, there is shown a schematic view of the artificial chemically synthesized filaments 4 implanted according to another embodiment of the present invention. As shown in FIG. 8, the hidden portions of the fixing thread 14 are 0.1 mm to 4 mm deep in the human scalp 2 and are spaced apart from each other by a distance D2 that ranges between 0.1 mm and 10 mm, and the exposed portions of the fixing thread 14 are spaced apart from each other by a distance D1 that ranges between 2.5 mm and 25 mm.

Figure 9:
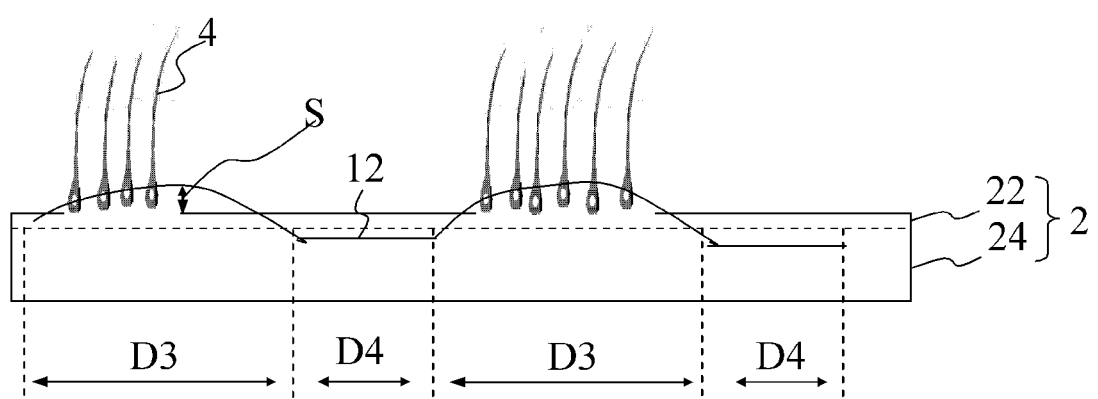
FIG. 9 is another schematic view of the artificial chemically synthesized filaments implanted according to the process flow described in FIG. 6.

Referring to FIG. 9, there is shown a schematic view of the artificial chemically synthesized filaments 4 implanted according to yet another embodiment of the present invention. As shown in FIG. 9, when pulled by the needle, the fixing thread 14 moves in a manner that the movement of the needle alternates between entering the epidermal layer 22 and the dermal layer 24 from outside the human scalp 2 and exiting the epidermal layer 22 and the dermal layer 24 to thereby leave the human scalp 2. As a result, the fixing thread 14 comprises the exposed portion above the human scalp 2 and the hidden portion inside the epidermal layer 22 and the dermal layer 24, wherein the exposed portion and the hidden portion alternate. As a result, the plurality of spaces S are formed between the human scalp 2 and the exposed portions of the fixing thread 14, respectively. A plurality of said fixing threads 14 are arranged within the recipient area of the human scalp 2. The exposed portions of the fixing thread 14 are spaced apart from each other by a distance D3 that ranges between 2.5 mm and 25 mm. The hidden portions of the fixing thread 14 are spaced apart from each other by a distance D4 that ranges between 0.1 mm and 10 mm. At the end of the hair transplantation operation, the artificial chemically synthesized filaments 4 are fixed to the human scalp 2. With the artificial chemically synthesized filaments 4 each being of a thread diameter ranging between 0.05 mm and 0.1 mm, the spaces S formed between the human scalp 2 and the exposed portions of the fixing thread 14, respectively, can accommodate a total of 25~50 said artificial chemically synthesized filaments 4. The aforesaid distances that separate the hidden portions of the fixing thread 14 enable sufficient air ventilation immediately above the recipient area of the human scalp 2 after hair transplantation.

Unlike the prior art, the present invention provides an artificial hair transplantation method whereby artificial chemically synthesized filaments are implanted into the epidermal layer and the dermal layer of the human scalp in a manner that the artificial chemically synthesized filaments thus implanted are approximately 0.4 mm deep in the human scalp (wherein, as a matter of fact, the epidermal layer is 0.1 mm to 0.7 mm thick, and the dermal layer is 3 to 5 times thicker than the epidermal layer). Hence, the artificial chemically synthesized filaments thus implanted lie at a small depth in the human scalp, the filament-receiving holes opened in the human scalp by the surgeon during the hair transplantation process are small and shallow and thus cause relatively little pain to the hair transplantation patient. Given a filament recipient area of just 1 cm² to 3 cm², hair restoration can be accomplished in a short period of time, such as a few hours. The artificial chemically synthesized filaments proposed by the present invention are of high strength and high fidelity, and are implanted into the human scalp by means of a therapeutic needle; hence, the artificial hair transplantation method of the present invention reduces transplant rejection and infection. Accordingly, the artificial hair transplantation method of the present invention is effective in hair restoration and hair replacement.

The present invention is disclosed above by preferred embodiments. However, persons skilled in the art should understand that the preferred embodiments are illustrative of the present invention only, but should not be interpreted as restrictive of the scope of the present invention. Hence, all equivalent modifications and replacements made to the aforesaid embodiments should fall within the scope of the present invention. Accordingly, the legal protection for the present invention should be defined by the appended claims.

What is claimed is:

1. An artificial hair transplantation method for performing hair transplantation limited to an epidermal layer and a dermal layer of a human scalp, the method comprising the steps of:
   (S11) providing an artificial chemically synthesized filament;
   (S12) providing a needle for pulling the artificial chemically synthesized filament and driving the artificial chemically synthesized filament to enter the epidermal layer and the dermal layer, and driving the needle to leave the epidermal layer and the dermal layer and stay above the human scalp such that the needle separates from the epidermal layer and the dermal layer, wherein the needle enables the artificial chemically synthesized filament to be present in the epidermal layer and the dermal layer simultaneously; and
   (S13) crossing and knotting the artificial chemically synthesized filament above the human scalp so as to form a knot at an appropriate point of the artificial chemically synthesized filament, followed by fixing the artificial chemically synthesized filament to the human scalp, wherein step S12 further comprises the sub-step of pushing the needle into the epidermal layer and the dermal layer to reach a predetermined depth therein, and the predetermined depth ranges between 0.1 mm and 4 mm.

2. The artificial hair transplantation method of claim 1, wherein the artificial chemically synthesized filaments with the knots appear in form of half synthetic filaments being two times as many as the artificial chemically synthesized filaments.

3. The artificial hair transplantation method of claim 1, wherein, after the knot is formed, the artificial chemically synthesized filament is knotted repeatedly to reinforce the implantation of the artificial chemically synthesized filament in the human scalp.

4. The artificial hair transplantation method of claim 1, wherein the artificial chemically synthesized filaments are implanted into a plurality of pseudo hair follicles above the human scalp in accordance with positions and the pattern of arrangement of a plurality of hair follicles in the dermal layer.

5. The artificial hair transplantation method of claim 4, wherein the pseudo hair follicles are spaced apart from each other by a distance ranging between 2 mm and 4 mm.

6. The artificial hair transplantation method of claim 5, wherein a plurality of said artificial chemically synthesized filaments are implanted into each of the pseudo hair follicles.

7. The artificial hair transplantation method of claim 6, wherein the artificial chemically synthesized filaments positioned at each of the pseudo hair follicles are spaced apart from each other by a distance that ranges between 0.5 mm and 1.5 mm.

8. The artificial hair transplantation method of claim 1, wherein the artificial chemically synthesized filament is made of at least one of green & white polyfilament chemical absorbable suture (EU-TEK/PGA), violet polyfilament chemical absorbable suture (Violet), plain catgut, chromic catgut, monofilament nylon, braided nylon, Unilene polypropylene suture, polyester suture, wire, silk, and twisted silk.

9. The artificial hair transplantation method of claim 1, wherein the needle is at least one of a reverse cutting needle, a regular cutting needle, a diamond point needle, and a premium reverse cutting.

10. An artificial hair transplantation method for performing hair transplantation limited to an epidermal layer of a human scalp, the method comprising the steps of:

(S61) providing an artificial chemically synthesized filament and a fixing thread;

(S62) providing a needle for pulling the fixing thread in a manner that movement of the needle alternates between entering the epidermal layer and the dermal layer from outside the human scalp and exiting the epidermal layer and the dermal layer to thereby leave the human scalp, wherein the fixing thread comprises a plurality of exposed portions above the human scalp, such that a plurality of spaces are formed between the human scalp and the exposed portions of the fixing thread, respectively; and (S63) passing the artificial chemically synthesized filaments through the spaces, followed by knotting the artificial chemically synthesized filaments in a manner that the knots thus formed are fixed to the fixing thread, thereby allowing the artificial chemically synthesized filaments to be fixed to the human scalp by means of the fixing thread, wherein step S62 further comprises the sub-step of pushing the needle into the epidermal layer and the dermal layer to reach a predetermined depth therein, and the predetermined depth ranges between 0.1 mm and 4 mm.

11. The artificial hair transplantation method of claim 10, wherein the artificial chemically synthesized filaments with the knots appear in form of half synthetic filaments being two times as many as the artificial chemically synthesized filaments.

12. The artificial hair transplantation method of claim 11, wherein, after the knot is formed, the artificial chemically synthesized filament is knotted repeatedly to reinforce the implantation of the artificial chemically synthesized filament in the human scalp.

13. The artificial hair transplantation method of claim 10, wherein the fixing thread comprises a plurality of exposed portions above the human scalp, and the exposed portions of the fixing thread are spaced apart from each other by a distance that ranges between 2.5 mm and 25 mm.

14. The artificial hair transplantation method of claim 13, wherein the fixing thread comprises a plurality of hidden portions inside the epidermal layer and the dermal layer, and the hidden portions of the fixing thread are spaced apart from each other by a distance that ranges between 0.1 mm and 10 mm.

15. The artificial hair transplantation method of claim 10, wherein the fixing thread comprises a plurality of exposed portions above the human scalp, and the exposed portions of the fixing thread are spaced apart from each other by a distance that ranges between 0.5 mm and 1.5 mm.

16. The artificial hair transplantation method of claim 10, wherein the artificial chemically synthesized filament is made of at least one of green & white polyfilament chemical absorbable suture (EU-TEK/PGA), violet polyfilament chemical absorbable suture (Violet), plain catgut, chromic catgut, monofilament nylon, braided nylon, Unilene polypropylene suture, polyester suture, wire, silk, and twisted silk.

17. The artificial hair transplantation method of claim 10, wherein the fixing thread is made of at least one of green & white polyfilament chemical absorbable suture (EU-TEK/PGA), violet polyfilament chemical absorbable suture (Violet), plain catgut, chromic catgut, monofilament nylon, braided nylon, Unilene polypropylene suture, polyester suture, wire, silk, and twisted silk.

18. The artificial hair transplantation method of claim 10, wherein the needle is at least one of a reverse cutting needle, a regular cutting needle, a diamond point needle, and a premium reverse cutting.

* * * * *